United States Patent [19]

Cocanower

[11] Patent Number: 5,334,167
[45] Date of Patent: Aug. 2, 1994

[54] MODIFIED NASOGASTRIC TUBE FOR USE IN ENTERAL FEEDING

[76] Inventor: David A. Cocanower, 4200 Bishop, Detroit, Mich. 48224

[21] Appl. No.: 154,980

[22] Filed: Nov. 19, 1993

[51] Int. Cl.⁵ ............................................. A61M 25/00
[52] U.S. Cl. ..................................... 604/280; 604/172; 604/54
[58] Field of Search ..................... 604/27, 28, 54, 164, 604/264, 265, 280, 281, 284, 171, 172

[56] References Cited

U.S. PATENT DOCUMENTS

| | | | |
|---|---|---|---|
| 883,583 | 3/1908 | Stallsmith . | |
| 1,596,754 | 8/1926 | Moschelle . | |
| 3,042,045 | 7/1962 | Sheridan . | |
| 3,058,472 | 10/1962 | Thornton . | |
| 3,153,415 | 10/1964 | Sheridan . | |
| 3,430,631 | 3/1969 | Abramson . | |
| 3,580,983 | 5/1971 | Jackson | 604/280 |
| 4,168,703 | 9/1979 | Kenigsberg | 604/280 |
| 4,180,076 | 12/1979 | Betancourt . | |
| 4,182,342 | 1/1980 | Smith . | |
| 4,270,542 | 6/1981 | Plumley . | |
| 4,275,724 | 6/1981 | Behrstock . | |
| 4,327,720 | 5/1982 | Bronson et al. . | |
| 4,543,089 | 9/1985 | Moss | 604/93 |
| 4,547,192 | 10/1985 | Brodsky et al. | 604/270 |
| 4,613,323 | 9/1986 | Norton et al. | 604/43 |
| 4,622,034 | 11/1986 | Shattuck | 604/179 |
| 4,634,425 | 1/1987 | Meer | 604/280 |
| 4,687,470 | 8/1987 | Okada | 604/171 |
| 4,705,709 | 11/1987 | Vailancourt | 428/36 |
| 4,778,448 | 10/1988 | Meer | 604/54 |
| 4,781,704 | 11/1988 | Potter | 604/270 |
| 4,790,832 | 12/1988 | Lopez | 604/283 |
| 4,795,442 | 1/1989 | Traflet | 604/179 |
| 4,801,294 | 1/1989 | Okada | 604/171 |
| 4,828,550 | 5/1989 | Kurimoto | 604/171 |
| 4,838,879 | 6/1989 | Tanabe et al. | 604/280 |
| 4,874,365 | 10/1989 | Frederick et al. | 604/54 |
| 4,878,762 | 11/1989 | Uddo et al. | 604/171 |
| 4,887,997 | 12/1989 | Okada | 604/54 |
| 4,895,562 | 1/1990 | Lopez | 604/48 |
| 4,955,375 | 9/1990 | Martinez | 604/280 |
| 4,986,815 | 1/1991 | Schneider | 604/180 |
| 4,998,919 | 3/1991 | Schnepp-Pesch et al. | 604/164 |
| 5,037,387 | 8/1991 | Quinn et al. | 604/51 |
| 5,057,091 | 10/1991 | Andersen | 604/270 |
| 5,057,093 | 10/1991 | Clegg et al. | 604/283 |
| 5,092,847 | 3/1992 | Pozzo | 604/170 |
| 5,152,756 | 10/1992 | Quinn et al. | 604/270 |
| 5,242,429 | 9/1993 | Nwaneri et al. | 604/270 |

FOREIGN PATENT DOCUMENTS 242051  10/1987  European Pat. Off. ............ 604/280

OTHER PUBLICATIONS

"Intragastric pH Measurement Using a Novel Disposable Sensor"; Intensive Care Med (1988) 14:232-235; Heath, et al.

Abstract: "Localization of Enteral Feeding Tube Placement by Intestinal Myoelectric Frequency"; Clinical Congress Abstracts; Cannon, et al.

*Primary Examiner*—John G. Weiss
*Attorney, Agent, or Firm*—Leydig, Voit & Mayer

[57] ABSTRACT

A nasogastric tube which includes a flexible, collapsible introducer sheath for facilitating guided gastric intubation of an enteral feeding tube. The collapsible sheath is made of thin polyvinyl chloride, is puncture and tear resistant, and is molded externally and lengthwise to a nasogastric tube. The sheath is open at its proximal and distal ends, and impregnated on its internal surface with water activated lubricant which allows for placement of a feeding tube into the stomach through the sheath of an already placed nasogastric tube.

22 Claims, 5 Drawing Sheets

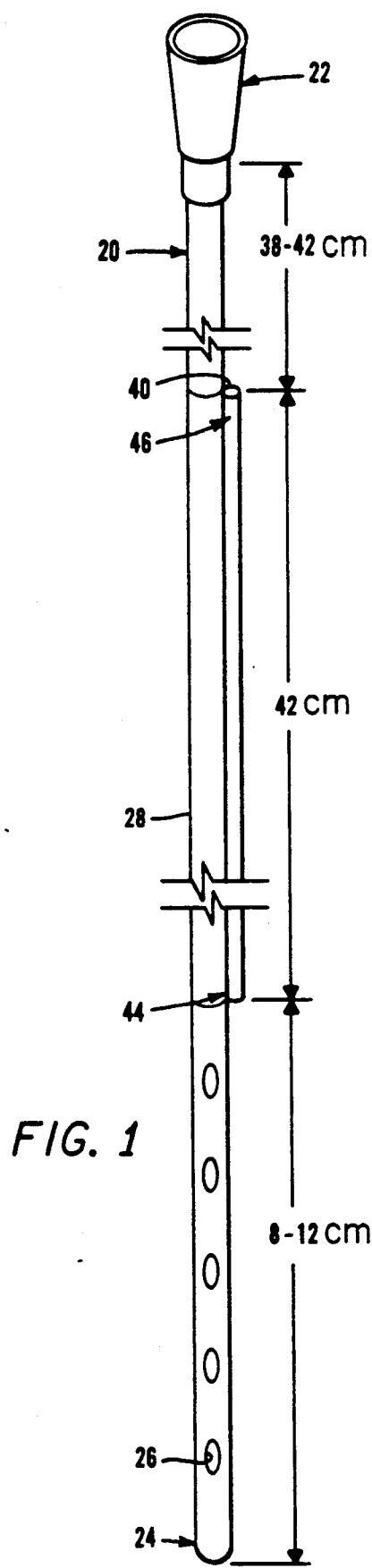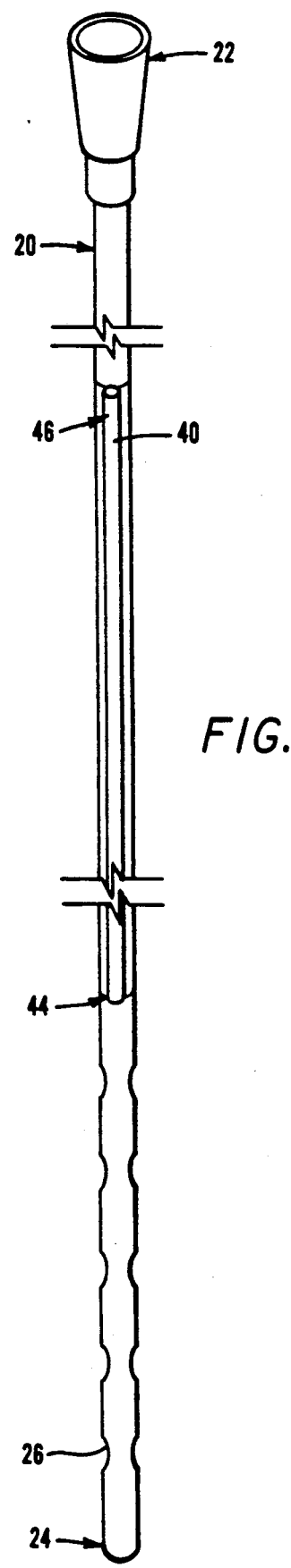

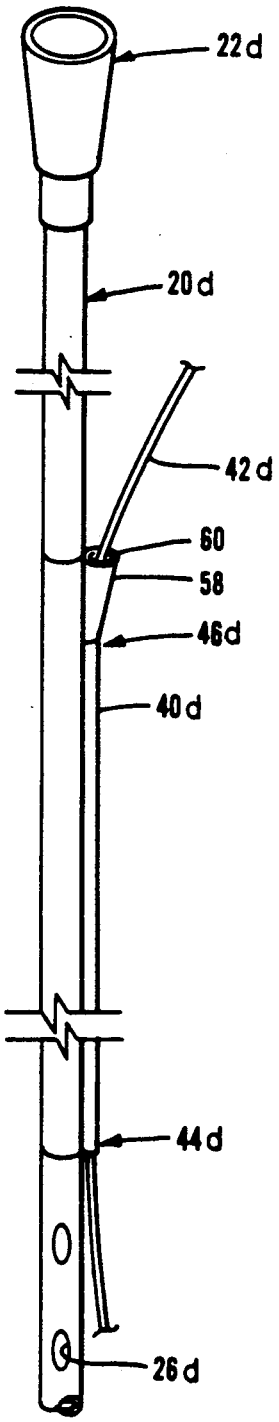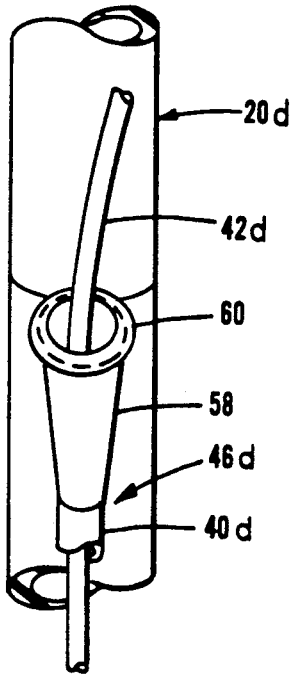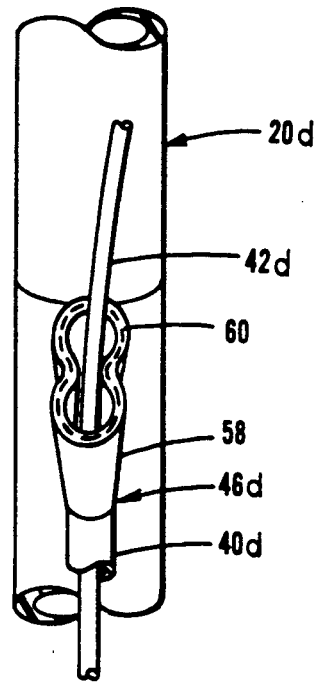
FIG. 12
FIG. 13a
FIG. 13b

MODIFIED NASOGASTRIC TUBE FOR USE IN ENTERAL FEEDING

FIELD OF THE INVENTION

The invention relates generally to enteral feeding tubes, and more specifically to placement of enteral feeding tubes into the stomach of a patient.

BACKGROUND OF THE INVENTION

Over the past twenty years, enteral nutrition has largely replaced parenteral nutrition as the preferred method of providing the metabolic needs of critically ill individuals. This is accomplished by administering specially formulated, liquid nutritional products through specially designed small bore enteral feeding tubes. While nutritional products used in enteral feeding vary in composition, they are formulated to satisfy the total nutritional needs of the patient.

Enteral feeding offers various advantages over parenteral feeding. Enteral feeding provides a more physiologic route of providing nutrition; by using the gut, it allows maintenance of mucosal barrier function, and permits healing of injured mucosa. Further, it is believed that enteral feeding prevents bacterial translocation through atrophic and injured mucosa, which is considered an important source of bacterial invasion in the pathogenesis of sepsis in some individuals. Additionally, the cost of enteral feeding, as well as the rate of associated complications, is lower than with parenteral feeding.

During the past twenty years, various advances have been made in the methods and equipment used in enteral feeding. Improvements have been made in the nutritional supplements themselves, as well as the devices by which the nutritional liquid is provided. Pump mechanisms have been developed for delivering the liquid nutrition, and these devices have been improved over the years.

Improvements have also been made in the feeding tubes utilized in enteral feeding. The use of various polymeric materials, such as polyurethane, in the manufacturing of feeding tubes has resulted in softer, and more flexible tubes, having reduced diameters. These features have resulted in greater patient comfort, and have enabled the feeding tubes to remain in position for longer periods of time, leading to increased acceptance of the use of feeding tubes.

Additionally, improvements in the distal end of the tubes have led to enhanced flow through the tube with fewer clogs. The use of weighted distal tips and stylets facilitates the nasogastric placement of lighter and less bulky tubes.

Although feeding tubes are sometimes passed orogastrically, most are currently passed nasogastrically. Generally, in placing a nasogastric feeding tube, the tube is first lubricated with a lubricant gel. The tube, along with a stylet, is then introduced into one of the nares, and advanced to the posterior pharynx. Once the tube is in the posterior pharynx, it is advanced through the esophagus so that the proximal end is at the nares or until enough tube has been passed to suggest gastric placement. The tube stylet is then removed. At any time, if insertion is felt to be outside of the alimentary tract, or if any firm resistance or patient discomfort is encountered, the tube is withdrawn, and reinsertion is attempted in either the same or the other nares. Placement into the stomach is verified by various physical examination maneuvers, aspirative tests, or radiograph. Once placement of the tube in the stomach or beyond has been verified, appropriate equipment is attached to the tube to deliver enteral nutrition.

Numerous problems may be encountered in the utilization of enteral feeding equipment and the delivery of liquid nutritional products. Among these problems are the ease and safety of various aspects of tube placement, issues of safety being the most important. Technical factors impact the ease and efficiency of tube placement and can affect patient comfort.

The risk of malplacement of feeding tubes is an important concern, and has been a major focus of medical literature describing complications of enteral feedings. Since the popularization of flexible, small bore feeding tubes, there have been more than 30 reports in the literature which describe aberrant placement of these tubes. The greatest occurrence of these reports concerns pulmonary malplacement. Feeding tubes are frequently malplaced into the lung due to the size and flexibility of the tubes, regardless of their use with stylets or guidewires. Risk factors for malplacement include endotracheal intubation, and a decreased sensorium.

Due to the risk of malplacement of feeding tubes, most institutions require verification of feeding tube placement prior to the initiation of feeding. The general view in the medical field is that physically examining patients by methods such as auscultation, and checking aspirate pH and myoelectric patterns are not adequate verification methods. The institutional policies of most hospitals therefore require that a widely-accepted and highly reliable test be performed to verify proper placement, wherein a radiograph which includes the thorax and upper abdomen is taken to ensure proper placement. Medical literature generally supports this view, and case reports on malplacement recommend this approach.

Compared to a feeding tube, a nasogastric (N-G) tube is considerably less difficult to place. An N-G tube is of relatively large diameter and less flexible, making it more difficult to pass into aberrant locations, such as a lung. Although reports of malplacement of N-G tubes exist, this is generally considered to be a very unusual occurrence.

An N-G tube is used diagnostically (e.g., pH testing of gastric fluid, evaluation of gastric contents in a GI hemorrhage) and therapeutically (e.g., decompression and removal of stomach contents, lavage, administration of medications). Nearly all patients in an Intensive Care Unit (ICU) will have an N-G tube placed for diagnostic and/or therapeutic reasons. Further, many patients on general medical and surgical wards have N-G tubes placed at some time during treatment.

In contrast to feeding tubes, verifying N-G tube placement is less difficult, given the caliber of the tube and enhanced ability to insufflate air and aspirate fluids (i.e., gastric). Radiographic verification is typically not necessary and not generally obtained to verify N-G tube placement. Rather, physical examination methods are typically used to verify placement. Moreover, the use of physical examination methods for N-G tube placement is supported by the literature.

In addition to safety concerns, technical difficulties may affect the ease and efficiency of feeding tube placement. For example, suitable sites to introduce nasoenteral feeding tubes may not be available, particularly in ICU patients. Additionally, structural variations in nares, posterior pharynx, and esophagus may likewise result in difficulties in the ease and efficiency of tube placement.

As indicated above, nearly all ICU patients have an N-G tube in place to facilitate management. Consequently, one nares remains for feeding tube placement. However, endotracheal tubes are often placed naso-tracheally, utilizing the available nares. Due to its large size, the placement of an endotracheal tube precludes passage of either an N-G tube or feeding tube through the same nares.

Although a feeding tube can be placed through a nares which already has an N-G tube in place, the placement is difficult for both practical and technical reasons. If an N-G tube is already in place, the friction created between the tubes makes it difficult to properly place a feeding tube in the same nares. Moreover, an N-G tube is larger and less flexible than a feeding tube, and is, therefore, generally easier to manipulate. Consequently, if a feeding tube is to be placed in the same nares as an N-G tube, the generally accepted procedure is to place the feeding tube first, then place the N-G tube, even though this may require that an N-G tube, which is already in place, be removed to allow this order of placement. Inasmuch as there is usually some delay in feeding tube placement once a patient enters an ICU, an N-G tube is generally already in place when the feeding tube is placed.

Even when a nares is available solely for feeding tube placement, certain disadvantages are associated with the use of this second site. Patients may have anatomic variations in nares, posterior pharynx, and esophageal anatomy. While these variations may not be troublesome with regard to the placement of a larger, less flexible N-G tube, they may cause considerable problems or preclude passing a flexible feeding tube.

Additionally, placement of a second tube in a new site, i.e., the second nares, raises issues of patient comfort. The patient must endure the discomfort associated with the process of insertion and manipulation of a second free-standing tube.

Finally, the risks associated with the placement of a second free-standing tube in a second site is compounded in patients with hematologic abnormalities, including coagulopathies, and platelet deficiencies.

The technical difficulties outlined above impact not only patient comfort and safety, but also physician utilization of enteral feeding. Difficulty in implementing naso-enteral feeding may result in delays in implementation of feeding, the use of alternate nutritional modalities that are more dangerous and expensive, such as parenternal nutrition, or foregoing nutritional support completely.

OBJECTS OF THE INVENTION

It is a primary object of the invention to provide a safe, reliable method and means by which an enteral feeding tube may be placed in a patient. A related object of the invention is to reduce the risk of malplacement of the feeding tube.

Another object is to provide an economical method and means for placing and verifying placement of an enteral feeding tube in a patient. An additional object is to eliminate the need for radiographic verification of placement.

Yet another object of the invention is to simplify the manner in which a feeding tube is placed. A related object is to provide a convenient method and means for placing a feeding tube.

A further object of the invention is to reduce patient discomfort associated with the placement of an enteral feeding tube.

BRIEF SUMMARY OF THE INVENTION

In accomplishing these and other objectives, the invention provides an N-G suction tube to which a flexible, introducer sheath is coupled to facilitate guided gastric intubation of the enteral feeding tube. The N-G tube equipped with the feeding tube introducer sheath is placed nasogastrically into a patient using current practice procedure. Proper gastric placement of the N-G tube is then verified through physical examination and aspirative techniques, according to current practice. When it is determined that enteral feeding is necessary, an enteral feeding tube is placed through the feeding tube introducer sheath, and advanced a distance considered adequate to reach the stomach and extend beyond the distal ends of the sheath and the N-G tube. The position of the feeding tube in the stomach is then verified using physical examination methods; it is currently felt that no confirmatory radiograph would be required. Once the position of the feeding tube is verified, feeding may be initiated.

The N-G tube may be of any commercial design, and typically comprises length markers, as well as a lengthwise radiopaque line. The sheath, which is flexible and collapsible, is coupled lengthwise to the outer surface of the N-G tube, along the tube surface opposite the radiopaque line. While the sheath may be of various lengths, the distal end of the sheath should not, in any event, occlude any of the N-G tube openings.

The feeding tube introducer sheath is preferably fabricated of an appropriate polymeric material or medical grade material that provides features of collapsibility, flexibility and puncture and tear resistance. The interior surface of the sheath is provided with an appropriate lubricant. In the preferred embodiment, the internal surface of the sheath is impregnated along its entire length with a water activated lubricant.

The risk of pulmonary malplacement of the feeding tube is negligible when the N-G tube introducer sheath is utilized. An N-G tube is relatively easily and accurately placed into the stomach, and is, therefore, rarely malplaced. Moreover, the position of an N-G tube may be easily and accurately verified through physical examination methods. Consequently, the use of an N-G tube introducer sheath to place a feeding tube virtually excludes pulmonary malplacement. This added element of safety is critical and addresses concerns regarding the use of small bore feeding tubes.

It is likely that no confirmatory radiograph would be required following feeding tube placement. As a result, the costs associated with feeding tube placement and verification of placement would be greatly reduced. Radiographic verification of feeding tube placement is expensive, costing approximately $100 per portable film. Additionally, radiographs are labor intensive, and are often repeated in verifying proper placement. Moreover, radiographs expose the patient to radiation.

Additionally, oro-gastric placement of a feeding tube, if necessary, is more convenient and easier by utilizing the N-G tube introducer sheath as compared to manipulating two free tubes (the conventional N-G tube and the conventional feeding tube) within the oropharynx. Utilization of the N-G tube sheath for feeding tube placement eliminates the need for a second entry site. By using the N-G tube with introducer sheath, one is able to take advantage of a needed tube (N-G) to help facilitate the placement of an additionally needed tube (feeding tube). Consequently, the health care worker deals with a composite of tubes, rather than two free tubes. The nares is traversed by a free tube only once and the second tube is placed through the sheath. As a result, the potential risks, such as patient discomfort, bleeding, trauma, which result from passing tubes through the nares are greatly reduced.

The use of the N-G tube introducer sheath also simplifies decisions concerning how best to utilize available sites. The health care worker must consider only the best nares through which to pass the tubes. Though use of an N-G tube with sheath does not eliminate potential anatomic difficulties encountered in patients, it simplifies placement in anatomically variant patients. The health care worker only encounters placement problems once, when the N-G tube with introducer sheath is placed.

These and other features and advantages of the invention will be more readily apparent upon reading the following description of a preferred exemplified embodiment of the invention and upon reference to the accompanying drawings wherein:

BRIEF DESCRIPTION OF THE DRAWINGS

FIG. 1 is a plan view of a nasogastric tube constructed in accordance with teachings of the invention;

FIG. 2 is a side view of the nasogastric tube of FIG. 1;

FIG. 12 is an elevational view of an alternate embodiment of the invention comprising an introducer sheath having an enlarged aperture.

FIGS. 13 a and 13b are enlarged fragmentary views of the sheath aperture in various positions.

Figure 4:
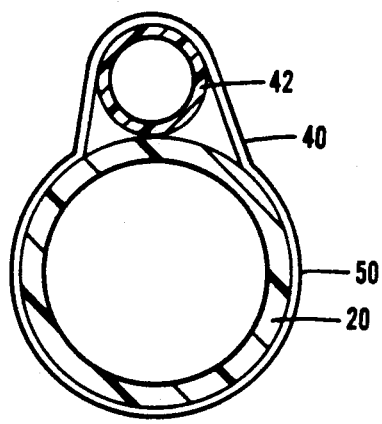
FIG. 4 is a cross-sectional view of the nasogastric tube and enteral feeding tube taken along line 4-4 in FIG. 3.

While the invention will be described in connection with certain preferred embodiments, there is no intent to limit it to those embodiments. On the contrary, the intent is to cover all alternatives, modifications, and equivalents included within the spirit and scope of the invention as defined by the appended claims.

DESCRIPTION OF THE PREFERRED EMBODIMENT

Turning now to the drawings, there is shown in FIG. 1, an N-G tube 20, which may be constructed according to the prior art. The N-G tube 20 is a clear, flexible, hollow tube, which is open at the proximal end 22, and closed and rounded at its distal end 24. The N-G tube 20 further has openings 26 which extend along opposite sides of the tube at its distal end 24, typically extending along the distal 6 cm. The N-G tube 20 may further include length markers (not shown), as well as a lengthwise continuous radiopaque line 28.

Figure 6:
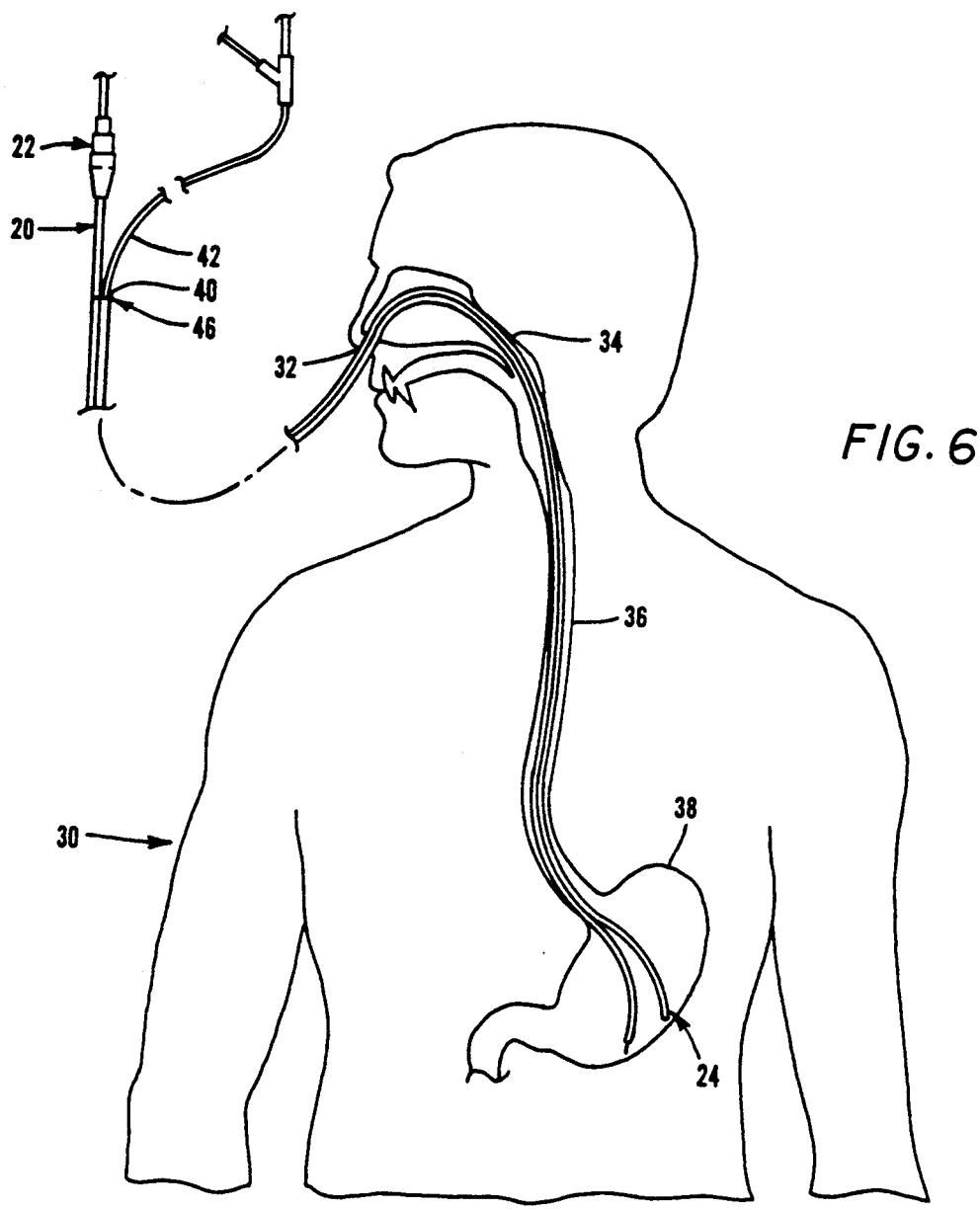
FIG. 6 is a view showing the nasogastric tube and enteral feeding tube disposed within the human body.

The N-G tube 20 may be placed in a patient 30 as shown in FIG. 6 by accepted techniques. The tube 20 is introduced into one of the nares 32, advanced to the posterior pharynx 34 and through the esophagus 36 into the stomach 38, the distal end 24 being disposed within the stomach 38. The open proximal end 22 of the tube 20 may received a syringe (not shown) or be hooked to a suction device (not shown). In this manner, the hollow tube and distal holes allow for instillation and aspiration.

Figure 3:
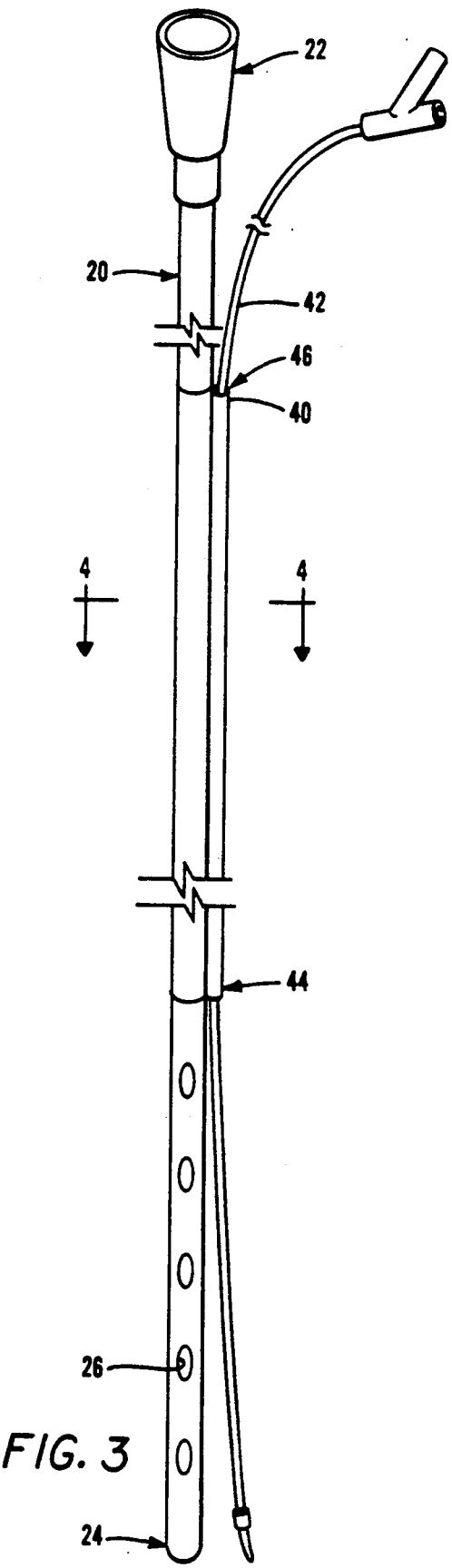
FIG. 3 is a plan view of the nasogastric tube of FIG. 1 having an enteral feeding tube disposed within the introducer sheath.

In accordance with the invention, the N-G tube is provided with a flexible, collapsible, introducer sheath 40 which is preferably used to facilitate guided gastric intubation of an enteral feeding tube 42. In use, the N-G tube 20 equipped with the feeding tube introducer sheath 40 is placed nasogastrically into a patient 30, as set forth above. Proper gastric placement of the N-G tube 20 is then verified through physical examination and aspirative techniques, according to current practice. When it is determined that enteral feeding is necessary, an enteral feeding tube 42 is placed through the sheath 40, and advanced a distance considered be adequate to reach the stomach 38 and extend beyond both the distal end 44 of the sheath 40, and the distal end 24 of the N-G tube 20, as shown in FIGS. 3 and 6. The position of the feeding tube 42 in the stomach 38 is then verified by any appropriate method. The currently preferred verification method is physical examination, as it is believed that a confirmatory radiograph would not be necessary. Once the position of the feeding tube 42 is verified, feeding may be initiated.

The sheath 40 is preferably fabricated of an appropriate polymeric material of medical grade material that provides features of collapsibility, flexibility and puncture and tear resistance. For example, polyvinyl chloride, polyethylene, and silicone are particularly suitable for fabricating the thin-walled construction of the sheath 40. Use of a collapsible material to form the sheath 40 allows the sheath 40 to collapse and conform to the outer surface of the N-G tube 20 when a feeding tube is not present. This allows for easier advancement of the N-G tube 20 during placement in a patient. It also provides for greater patient comfort as the N-G tube 20, with attached sheath 40, has the smallest possible diameter.

Further, the N-G tube 20 may be provided at its distal tip 24 with pH sensor, such as an antimony/graphite pH sensor as disclosed in U.S. Pat. No. 4,561,963.

In order to facilitate feeding tube entry and movement through the sheath 40, the interior surface of the sheath 40 is provided with an appropriate lubricant. In the preferred embodiment, the internal surface of the sheath 40 is impregnated along its entire length with a water activated lubricant. In this way, when enteral feeding is desired, water is passed through the sheath 40 of the positioned N-G tube 20/sheath 40 to activate the lubricant along the internal surface of the sheath 40. The feeding tube 42 may then be easily passed within the sheath 40 and properly positioned within the stomach 38.

The sheath 40 is coupled lengthwise to the outer surface of the N-G tube 20, along the tube surface opposite the lengthwise radiopaque line 28. While the sheath 40 may be various lengths, the distal end 44 of the sheath 40 should not, in any event, occlude any of the N-G tube openings 26. Further, the length of sheath 40 should be chosen such that its distal end 44 is disposed distally of the epiglottis when the N-G tube 20 is properly positioned. This ensures that introduction of an enteral feeding tube 42 will not result in malplacement of feeding tube 42 into the proximal airways. In the preferred embodiment shown in FIGS. 1 and 2, a total N-G tube length of 130 cm is assumed. In this embodiment, the proximal end 46 of the sheath 40 preferably begins no more proximal than 38 cm, and no more distal than 42 cm from the proximal end 22 of the N-G tube 20; the distal end 44 of the sheath 40 preferably begins no more distal than 8–12 cm from the N-G tube tip or distal end 24.

The internal diameter of the sheath 40 would preferably be of sufficient size to accommodate either the currently available small bore feeding tubes (6–12 F), or the feeding tube bolus, whichever is larger. Alternatively, the sheath could be made to accommodate only selected tube sizes.

Figure 5:
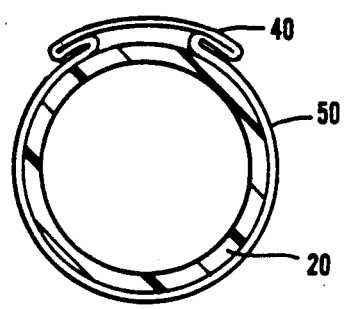
FIG. 5 is a cross-sectional view of the nasogastric tube shown in FIG. 4, and showing the sheath for the enteral feeding tube in a collapsed configuration.

The sheath 40 may be fabricated using any appropriate method. In the preferred manufacturing process, the sheath 40 would be created by enveloping an N-G tube 20 within a sleeve 50 or cylinder of flexible, clear polyvinyl chloride, as shown in FIG. 4. The sleeve 50 would be of sufficient diameter to surround both the N-G tube 20, and the largest diameter portion of a feeding tube 42. The sleeve 50 would then be secured by molding or the like to approximately 80% of the circumference of the N-G tube 20. As shown in FIG. 4, the unattached portion of the sleeve 50 along with the remaining 20% of the circumference of N-G tube would be sufficient to form the sheath 40. The same N-G tube 20 is shown in FIG. 5. There, however, the sheath 40 is shown in its collapsed configuration, wherein it conforms to the exterior surface of N-G tube 20.

Figure 7:
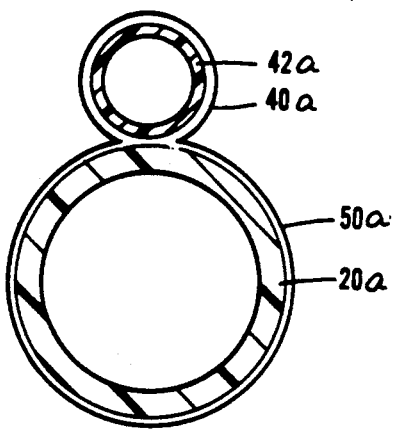
FIG. 7 is a cross-sectional view of another embodiment of the invention showing an alternate attachment of the introducer sheath to the nasogastric tube.
Figure 8:
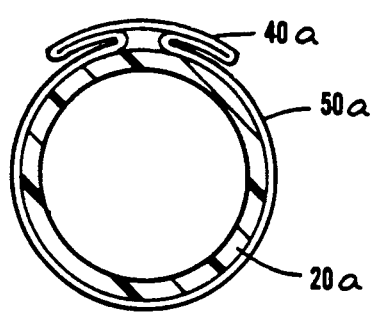
FIG. 8 is a cross-sectional view of the nasogastric tube shown in FIG. 7, and showing the sheath for the enteral feeding tube in a collapsed configuration.

An alternate embodiment of the invention is shown is FIG. 7. This embodiment incorporates a slightly larger diameter sleeve 50a, which is secured to substantially the entire circumference of the N-G tube 20a. In this way, the sleeve 50a forms substantially the entire sheath 40a. FIG. 8 shows the same embodiment, but with the sheath 40 in its collapsed, conforming configuration.

Figure 9:
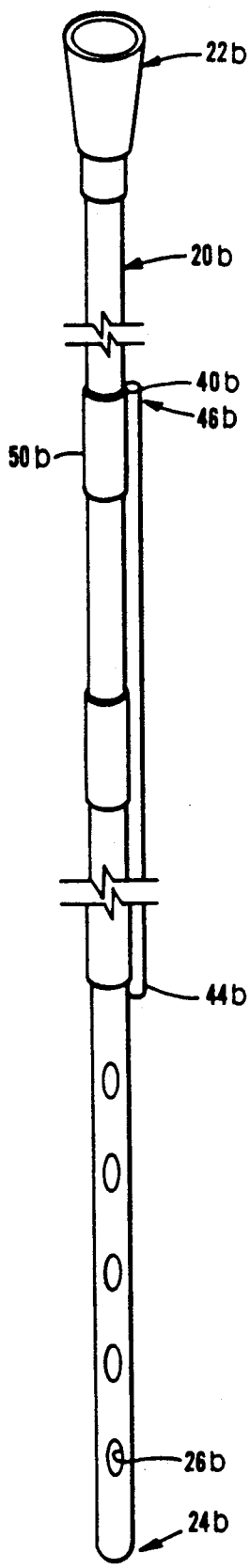
FIG. 9 is an elevational view of another embodiment of the invention showing an alternate attachment of the introducer sheath to the nasogastric tube.

In another embodiment of the invention, the sheath 40b may be constructed separately. The sheath 40b includes a lumen through which a feeding tube may be placed, and a variable number of longitudinally noncontinuous sleeves 50b through which the N-G tube may be passed. Prior to placing the N-G tube 20b in the patient, the N-G tube 20b is placed through the sleeves 50b and the sleeves secured thereto, as shown in FIG. 9.

Figure 10:
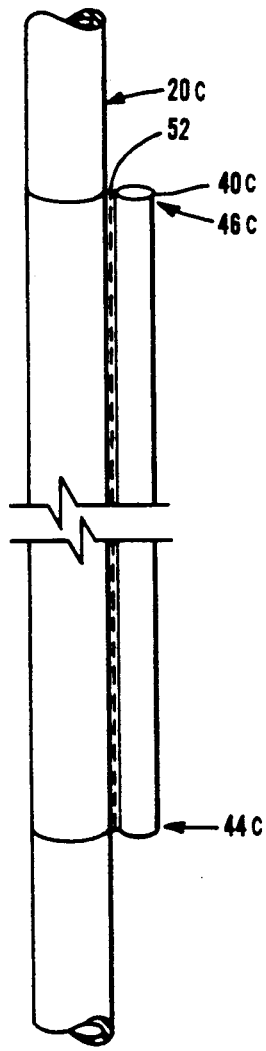
FIG. 10 is a fragmentary view of another embodiment of the invention having a line of weakness at the attachment between the introducer sheath and the nasogastric tube.
Figure 11:
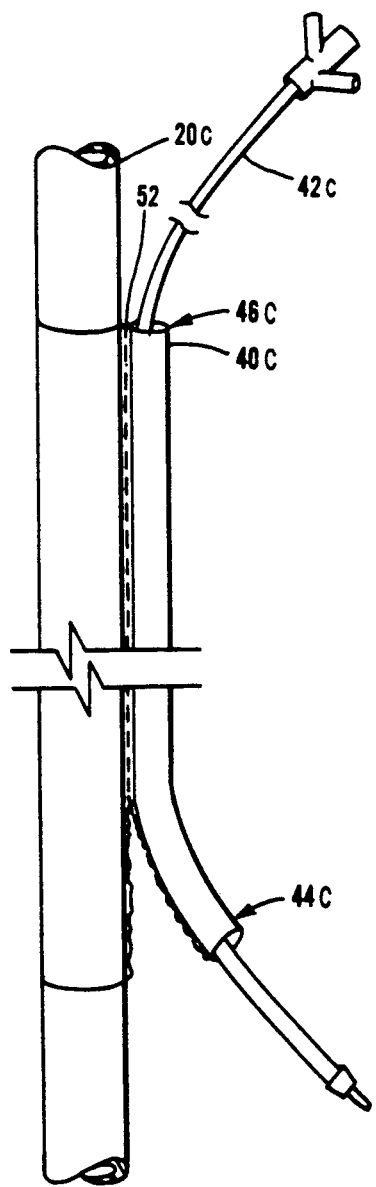
FIG. 11 is a fragmentary view of the embodiment shown in FIG. 10 having the introducer sheath partially separated from the nasogastric tube.

In order to permit the N-G tube 20c to be removed from the patient once the N-G tube 20c and feeding tube have been placed, the invention may be provided with a means by which the sheath 40c and the N-G tube 20c may be separated. In the embodiment shown in FIGS. 10 and 11, the sheath 40c is provided with a longitudinally extending line of weakness 52 substantially adjacent its attachment at the N-G tube 20c. The separation of the sheath 40c from the N-G tube 20c may be initiated by the withdrawal of a string (not shown) or the like.

In order to facilitate easy introduction of the feeding tube 42d into the sheath 40d, the sheath 40d may be provided with an "introducer hub" 58 at its proximal end 46d (FIGS. 12, 13a, 13b). The hub 58 may be fabricated by any desired method. Preferably, the hub 58 is molded or glued directly to the N-G tube 20d, and attached directly to the plastic sheath 40d. The introducer hub 58 has a slightly greater inner and outer diameter than the sheath 40d and tapers into the sheath 40d.

The hub 58 preferably consists of a pliable ring 60 in the nature of a wire support that is rubber coated. By applying pressure along the circumference of the ring 60, the ring 60 can be squeezed into an oval, or "8-shaped" structure, as shown in FIG. 13b. In this way, the feeding tube 42d may be secured at the hub without compromising tube flow. It will be appreciated that by applying additional pressure at the ends of the oval or "8" portion of the ring 60, the ring would resume its previous rounded shape in a manner consistent with the pressure applied.

The N-G tube 20d may further be provided with a plastic adaptor (not shown) disposed adjacent to the end of the hub 58. The distal end of the adaptor is designed to fit snugly into the hub 58. The proximal end of the adaptor is designed to accommodate a 20 cc (or larger) syringe.

It is to be understood that any allowed claims based on this application are to be accorded a range of equivalence commensurate in scope with the advance over the prior art.

I claim as my invention:

1. A nasogastric tube having distal and proximal ends and openings along its distal end, comprising, in combination, an introducer sheath having distal and proximal ends, the sheath extending longitudinally along and being coupled to the nasogastric tube, the sheath distal end not obstructing the nasogastric openings, the sheath defining a longitudinally extending lumen of sufficiently large inner diameter to permit an enteral feeding tube to be passed therethrough, the sheath being of a flexible construction and being collapsible against the nasogastric tube.

2. The nasogastric tube of claim 1 wherein the sheath lumen is lubricated.

3. The nasogastric tube of claim 1 wherein the sheath lumen is impregnated with a water activated lubricant.

4. The nasogastric tube of claim 1 wherein the sheath is fabricated from a polymeric material.

5. The nasogastric tube of claim 1 wherein the sheath is fabricated from polyvinyl chloride.

6. The nasogastric tube of claim 1 wherein the sheath is glued to the nasogastric tube.

7. The nasogastric tube of claim 1 wherein the sheath is molded to the nasogastric tube.

8. The nasogastric tube of claim 1 further comprising a sleeve of flexible construction having a diameter larger than the diameter of the nasogastric tube, the sleeve having a portion circumferentially attached to the nasogastric tube.

9. The nasogastric tube of claim 8, wherein the sleeve is circumferentially attached to the nasogastric tube over 80% of the circumference of the nasogastric tube, the remaining 20% of the nasogastric tube and the unattached portion of the sleeve forming the sheath.

10. The nasogastric tube of claim 8, wherein the sleeve is circumferentially attached to the nasogastric tube over substantially the entire circumference of the nasogastric tube, the unattached portion of the sleeve forming the sheath.

11. The nasogastric tube of claim 1, wherein the sheath is longitudinally attached to a sleeve, the sleeve being adapted to be received upon, and secured to, the nasogastric tube.

12. The nasogastric tube of claim 11, wherein the sleeve comprises a series of longitudinally non-continuous sections.

13. The nasogastric tube of claim 1 further comprising a hub at the proximal end of the sheath, the hub defining an entrance to the lumen.

14. The nasogastric tube of claim 13 wherein the hub comprises a pliable ring at its proximal end.

15. The nasogastric tube of claim 14 wherein the pliable ring comprises a deformable wire, the wire being rubber coated.

16. The nasogastric tube of claim 15 wherein the wire may be deformed to reduce the width of the entrance to the lumen.

17. The nasogastric tube of claim 1, wherein the sheath is collapsible to conform to an exterior surface of the nasogastric tube.

18. The nasogastric tube of claim 1, wherein the sheath has a distal extent, such that the distal end of the sheath is located distally of a patient epiglottis when the nasogastric tube is properly placed.

19. A method for introducing an enteral feeding tube into a patient, comprising the steps of
placing a nasogastric tube to which an introducer sheath is coupled through the nares and esophagus of the patient and into the stomach,
verifying the proper placement of the nasogastric tube,
placing the enteral feeding tube through the sheath and into the stomach,
verifying placement of the feeding tube.

20. The method of introducing an enteral feeding tube into a patient as claimed in claim 19 further comprising the step of passing water through the sheath to activate lubricant along the inner surface of the sheath prior to placing the enteral feeding tube.

21. The method of introducing an enteral feeding tube into a patient as claimed in claim 19 wherein the step of verifying the placement of the nasogastric tube includes physically examining the placement.

22. The method of introducing an enteral feeding tube into a patient as claimed in claim 19 wherein the step of verifying the placement of the enteral feeding tube includes physically examining the placement.

* * * * *